United States Patent
Blanck et al.

(10) Patent No.: US 7,601,696 B1
(45) Date of Patent: Oct. 13, 2009

(54) OCT-1 AS AN ONCOPROTEIN AND USE OF NUCLEIC ACID INHIBITORS OF OCT-1 FOR CANCER TREATMENT

(75) Inventors: George Blanck, Tampa, FL (US); Kimberly Palubin, Atlanta, GA (US); Aaron Osborne, Tampa, FL (US)

(73) Assignee: University of South Florida, Tampa, FL (US)

( * ) Notice: Subject to any disclaimer, the term of this patent is extended or adjusted under 35 U.S.C. 154(b) by 551 days.

(21) Appl. No.: 10/711,101

(22) Filed: Aug. 23, 2004

Related U.S. Application Data

(60) Provisional application No. 60/481,275, filed on Aug. 22, 2003.

(51) Int. Cl.
*A61K 31/70* (2006.01)
*C07H 21/04* (2006.01)
*C12N 15/00* (2006.01)

(52) U.S. Cl. .................. 514/44; 536/23.1; 536/24.5; 435/320.1

(58) Field of Classification Search .................. None
See application file for complete search history.

(56) References Cited

U.S. PATENT DOCUMENTS 5,747,250 A 5/1998 Gruss et al.

OTHER PUBLICATIONS

Opalinska et al. Nature Reviews Drug Discovery, 2002, vol. 1, p. 503-514.*
Weiser et al. Molecular Biology of the Cell 1997, vol. 8, pp. 999-1011.*
Dent et al. Journal of Biological Chemistry 1991, vol. 266, pp. 20888-20892.*
Coenjaerts, Frank E.J. et al., The Oct-1 POU domain stimulates adenovirus DNA replication . . . , The EMBO Journal, 1994, 5401-5409, 13(22),Oxford University Press.
Hinkley, Craig et al., Histone H2B Gene Transcription during Xenopus Early Development Requires Functional Cooperation,Molecular and Cellular Biology, 1992, 4400-4411, 12(10).
Lakin, N.D. et al., Down Regulation of the octamer binding protein Oct-1 during growth arrest, Molecular Brain Research, 1995, 47-54, vol. 28.
Matheos, Diamanto D. et al., Oct-1 Enhances the In Vitro Replication of a Mammalian Autonomously Replicating DNA Sequence, J. of Cellular Biochemistry, 1998. 309-327. vol. 68.
Shona Murphy, Differential in vivo activation of the class II and class III snRNA genes by the POU-specific domain of Oct-1, Nucleic Acids Research, 1997, 2068-2076, 25(11).
Qin, Xiao-Feng et al., Transformation by homeobox genes can be mediated by selective transcriptional repression, The EMBO Journal, 1994, 5967-5976, 13(24), Oxford University.
Van Leeuwen, Hans C. et al., The Oct-1 POU Homeodomain Stabilizes the Adenovirus Preinitiation Complex, J. of Biological Chemistry, 1997, 3398-3405, 272(6).
Osborne, Aaron et al., Histone Deacetylase Activity Represses Gamma Interferon-Inducible HLA-DR Gene Expression . . . , Molecular and Cell Biology, 2001, 6495-6506, 21(19).

* cited by examiner

*Primary Examiner*—Tracy Vivlemore
(74) *Attorney, Agent, or Firm*—Michele L. Lawson; Smith & Hopen, P.A.

(57) ABSTRACT

Oct-1 is shown to be an oncoprotein because of its known role as an activator of the histone H2B gene and the importance of this gene during DNA synthesis. To determine the role of Oct-1 as an oncoprotein, the cell line 5637 (ATCC HTB9) was transfected with the vector pcDNA3 containing full length, antisense Oct-1 cDNA. This cell line is Rb-defective and has been shown to have increased Oct-1 binding activity as compared to Rb reconstituted clones. After transfection, Oct-1 antisense clones were grown and assayed for the loss of oncogenic characteristics as compared to control transformants.

7 Claims, 8 Drawing Sheets

FIG 2

Table of Densitometry Results for Oct-1 and Actin Western Blots

|        | C1  | C2  | A1  | A2  | A3  | A4  | A5  |
|--------|-----|-----|-----|-----|-----|-----|-----|
| Oct-1  | 154 | 122 | 54  | 118 | 131 | 151 | 158 |
| Actin  | 38  | 66  | 102 | 104 | 108 | 135 | 140 |
| Ratio  | 4.1 | 1.8 | 0.5 | 1.1 | 1.2 | 1.1 | 1.1 |
| % of C1| 100 | 46  | 13  | 28  | 30  | 28  | 28  |

A1 Intensity = 2077         C1 Intensity = 1129

A = Oct-1 Antisense A1    B = Oct-1 Control C1

Colony growth in 0.2% serum

A1           C1

US 7,601,696 B1

OCT-1 AS AN ONCOPROTEIN AND USE OF NUCLEIC ACID INHIBITORS OF OCT-1 FOR CANCER TREATMENT

CROSS REFERENCE TO RELATED APPLICATION

This application claims priority to U.S. Provisional Patent Application No. 60/481,275 filed on Aug. 22, 2003.

STATEMENT OF GOVERNMENT INTEREST

This work has been supported by National Institutes of Health grant R01 CA81497.

BACKGROUND OF THE INVENTION

Oncoproteins, the products encoded by oncogenes, can induce cancer in animals and transform normal cells in culture to become cancerous cells. Many oncoproteins are either derivatives of, or identical to, normal cellular proteins that regulate cell growth and division. Oncoproteins arise by two means. First, a mutation in the DNA sequence encoding a normal cellular protein can result in a mutant protein and a subsequent loss of cellular growth control. Second, a wild-type protein can be expressed at abnormally high levels or at inappropriate times due to a change in transcriptional regulation.

Oncoproteins induce changes in the growth characteristics of cells, resulting in tumor formation if these cells are injected into animals. An alteration that leads to increased tumor-forming capacity is termed a "malignant transformation." Often, transformation requires the synergistic effect of multiple oncogenes acting at once rather than a single mutation. The result of malignant transformation is generally cell immortality. When normal cells become damaged, hazardous, or superfluous, they undergo a programmed cell death known as apoptosis. A cell's mortality is believed to be an outcome of the differentiation of a dividing stem cell into an end-stage, non-dividing cell. Immortal cancerous cells may block this differentiation and remain in a continually dividing state, resulting in unlimited growth potential. Other characteristics of transformed cells include alterations in growth parameters and cell behavior, alterations at the cell surface, loss of cytoskeletal elements, secretion of transforming growth factors and proteases, and altered gene transcription. Transformed cells continue to divide when a normal cell would not, resulting in an increased saturation density in culture. Other changes include decreased growth factor and hormone requirements, deficiency in capacity for growth arrest, anchorage independent growth, a loss of contact inhibition, and altered cellular morphology.

Growth factors, growth factor receptors, intracellular signal transducers, nuclear transcription factors, and cell-cycle control proteins are some common oncoprotein candidates. Growth factors exist extracellularly and function as ligands for their associated receptors. The binding of a growth factor to its receptor normally induces a response that will initiate cell division. The receptor can be either intracellular, requiring a steroid or hormone growth factor, or bound to the cell membrane. When a membrane bound receptor contacts its ligand, the receptor stimulates a cascade response known as signal transduction. Signals are usually transmitted by the phosphorylation of numerous proteins by an activated kinase. The end result of this process is often regulation of gene transcription through the activation or inactivation of nuclear transcription factors by a change in the phosphorylation state. Transcription factors exert control over gene regulation by binding to DNA at specific sequence motifs within the promoters or enhancers of target genes.

Oct-1 is a ubiquitously expressed transcription factor that binds to an eight nucleotide sequence (ATTTGCAT) in the promoters and enhancers of a number of genes. It is a member of a family of transcription factors containing a POU domain, a 155 to 162 amino acid region which consists of a bipartite DNA-binding domain. This domain contains both an N-terminal $POU_S$ sub-domain and a C-terminal $POU_{HD}$ homeodomain. Oct-1 has been shown to regulate the transcription of many genes, including those encoding small nuclear RNAs, immunoglobulin, and the histone, H2B. Histones are essential for DNA synthesis and play an important role in controlling cell cycle progression. During the S phase of the cell cycle, transcription of the H2B histone gene requires the interaction of Oct-1 with its binding motif in the H2B promoter. In developing frog embryos undergoing rapid division, it has been shown that Oct-1 must be bound to the octamer motif, along with other factors bound to their respective sites, for maximal H2B transcription. This effect is not due to an increase in the DNA binding affinity of Oct-1, but rather to changes in transcription factor interactions at the octamer motif and at the CCAAT regulatory element in the promoter. In addition, it has been shown that Oct-1 is phosphorylated at a site in the homeodomain upon entering mitosis. This phosphorylation reduces the ability of Oct-1 to bind DNA. As cells exit mitosis, Oct-1 is subsequently dephosphorylated, thereby restoring its DNA binding affinity. These observations are consistent with the transcriptional inhibition at several Oct-1 regulated genes during mitosis, again illustrating the protein's importance in cell cycle control.

Oct-1 also plays a role in DNA synthesis in adenoviral replication. Upon infection with an adenovirus, the binding activity of Oct-1 is stimulated. This most likely occurs due to a decrease in phosphorylation of Oct-1 resulting in an increase in the level of the active protein. Octamer motifs are found in the viral terminal repeat sequences, which are important for the initiation of DNA replication. Indeed, it was shown previously that Oct-1 increases DNA replication in the adenovirus up to six-fold due to increased initiation frequency.

SUMMARY OF THE INVENTION

It is desirable to know the bases for cancer development to identify a target for drug development. The present invention provides a convenient assay allowing for the function of Oct-1 for testing anti-cancer therapeutics. For example, the binding of Oct-1 to DNA, which can be easily tested in the lab, facilitates tumor development. Thus, drugs that prevent the binding of this protein to DNA would be candidates for anti-cancer therapeutics.

The present invention presents Oct-1 to be an oncoprotein because of its known role as an activator of the histone H2B gene and the importance of this gene during DNA synthesis. To determine the role of Oct-1 as a possible oncoprotein, the cell line 5637 (ATCC HTB9) was transfected with the vector pcDNA3 containing full length, antisense Oct-1 cDNA. This cell line is Rb-defective and has been shown to have increased Oct-1 binding activity as compared to Rb reconstituted clones. After transfection, Oct-1 antisense clones were grown and assayed for the loss of oncogenic characteristics as compared to control transformants.

The present invention can be used to screen for drugs that could inhibit tumor growth. Also, the present invention could be used to diagnose and subclassify certain tumors for prognosis.

BRIEF DESCRIPTION OF THE DRAWINGS

For a fuller understanding of the nature and objects of the invention, reference should be made to the following detailed description, taken in connection with the accompanying drawings, in which:

FIG. 2 is a table representing the densitometry measurements on the Oct-1 (first row) and Actin (second row) Western Blot of the seven transformants. The third row is a calculated ratio of Oct-1 to actin based on the densitometry readings. The transformants A1 and C1 had the greatest numerical difference in intensity, with an eight-fold decrease in Oct-1 production in the A1 clone. In the fourth row of the table, the level of Oct-1 expression in each clonal cell line was taken as a percentage of C1;

FIG. 3 depicts this trend;

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

To determine the role of Oct-1 as a possible oncoprotein, the cell line 5637 (ATCC HTB9) was transfected with the vector pcDNA3 containing full length, antisense Oct-1 cDNA. This cell line is Rb-defective and has been shown to have increased Oct-1 binding activity as compared to Rb reconstituted clones. After transfection, Oct-1 antisense clones were grown and assayed for the loss of oncogenic characteristics as compared to control transformants.

Figure 1:
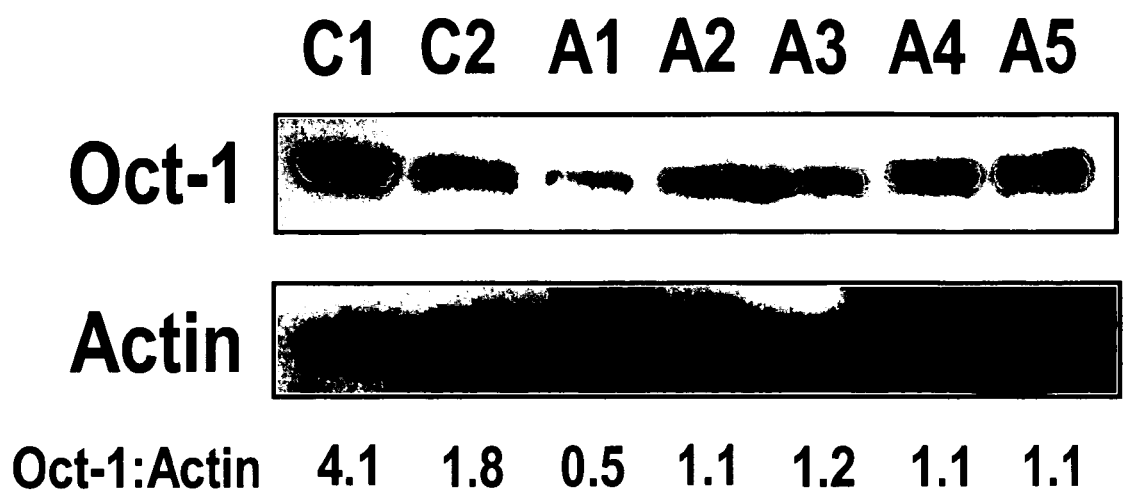
FIG. 1 illustrates the results of the Oct-1 and actin Western Blot depicting the two control transformants (C1, C2) and the five Oct-1 antisense transformants (A1 through A5). The Oct-1 to Actin ratio below each band was determined using densitometry measurements, as seen in the following figure. The transformant A1 had the most obvious reduction in Oct-1 levels according to the Western, while C1 had the highest level of expression of Oct-1.
Figure 3:
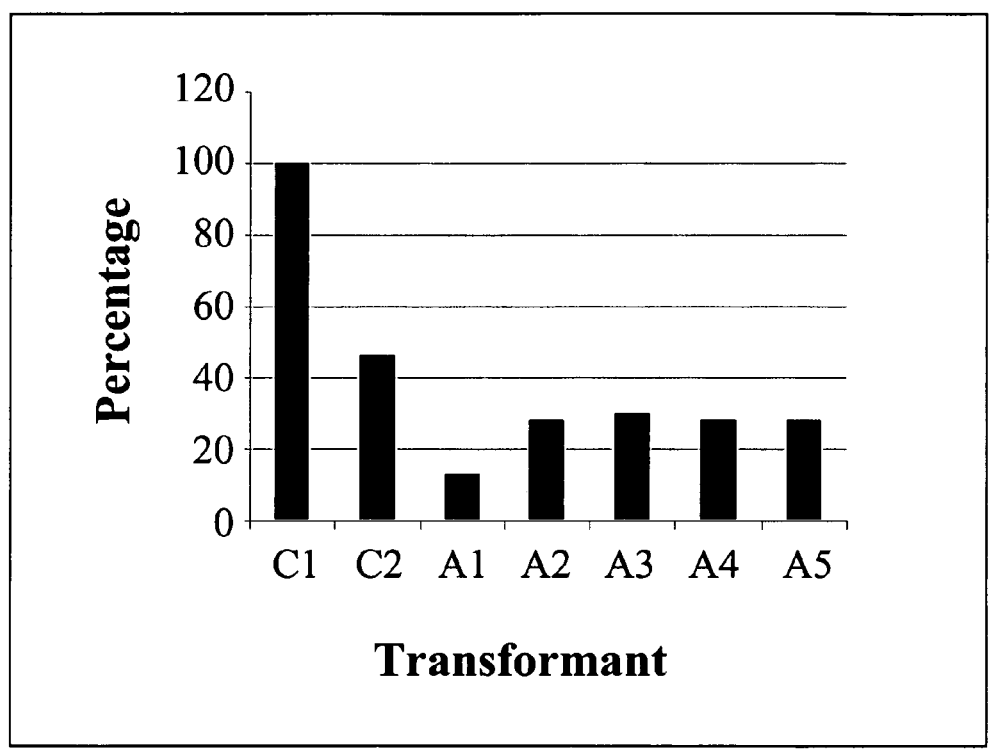
FIG. 3 illustrates the densitometry quantifications on the Oct-1 and actin Western Blot of the seven transformants. In the fourth row of the table shown in FIG. 2, the level of Oct-1 expression in each clonal cell line was taken as a percentage of C1.

Results of the Western Blot indicated a decreased level of Oct-1 present in cell lines that were transfected with the plasmid pAS-Oct-1 versus cells transfected with only pcDNA3 as shown in FIG. 1. In particular, the clone A1 had the most visually significant reduction in Oct-1 as compared to C1 and C2 according to the Western. The actin blot revealed an increased amount of actin in the antisense transformants as compared to lower actin levels in the controls. Therefore, the reduction of Oct-1 in the antisense transformants was more significant than the reduction evidenced from the Oct-1 blot alone. Densitometry readings were taken to measure the intensity of both the Oct-1 and actin bands from the Western, as shown in the table of FIG. 2. Results were recorded for each, and a ratio of Oct-1 to actin was calculated and used as a standard measure of the Oct-1 reduction. The two clones representing the greatest difference in Oct-1 levels were A1 (Oct-1:actin ratio 0.5) and C1 (Oct-1:actin ratio 4.1). This is equivalent to an eight-fold difference in Oct-1 expression in the two cell lines. The Oct-1 to actin ratio for the second control, C2, was 1.8, indicating Oct-1 levels four times higher than those in A1. The amount of Oct-1 expressed in each cell line was taken as a percentage of C1 and quantified, as shown in FIG. 3.

Figure 4:
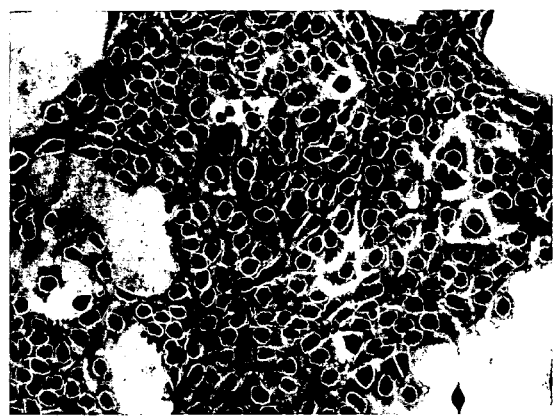
FIG. 4 illustrates images used by Metamorph to determine the average intensity of Oct-1 nuclear staining in the antisense transformant A1 and the control transformant C1. Note the darker nuclei present in C1 versus A1. The numerical averages are seen below each representative image.
Figure 4:
Figure 5:
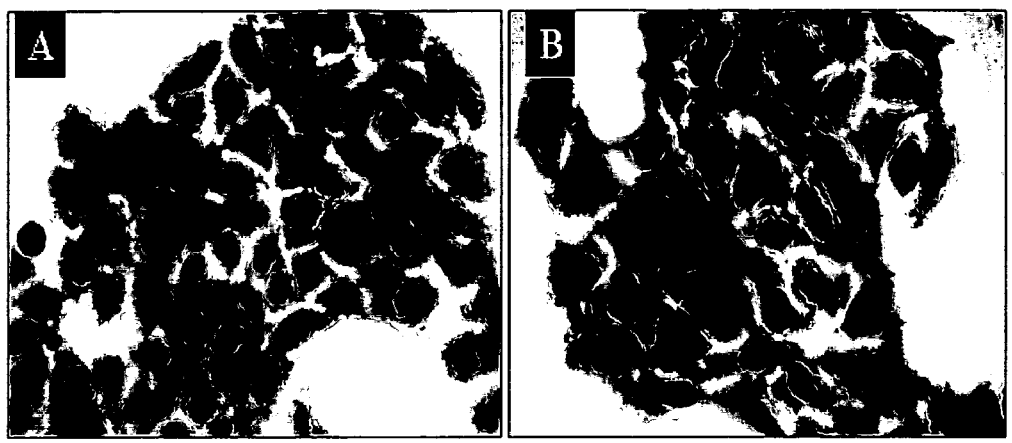
FIG. 5 illustrates Oct-1 antisense A1 and control C1 transformants evaluated for nuclear Oct-1 staining via visualization. The control has nuclei that are more intensely stained for Oct-1, while A1 has relatively blue nuclei. This is consistent with the Western and Metamorph results.

Oct-1 antisense and control transformants (A1, A2, A3, C1, C2) analyzed for nuclear Oct-1 staining via immunohistochemistry were quantified using the image analysis program Metamorph. Thirty individual cells were examined for nuclear Oct-1 staining intensity in randomly chosen fields. Each field was autoexposed to obtain the greatest linear range of color from white to black. The program measured black as the lowest intensity, with pure black counted as a value of zero. Lighter cells produced a higher intensity reading. The antisense transformant A1 (intensity reading 2077) had a greater intensity reading than C1 (intensity reading 1129), indicating a decrease of Oct-1 in the nucleus. FIG. 4 shows the images used by Metamorph to determine the average intensity of Oct-1 nuclear staining in the antisense transformant A1 and the control transformant C1. Note the darker nuclei present in C1 versus A1. The numerical averages are seen below each representative image. Digital photographs of both slides A1 and C1 were consistent with the Western Blot and image analysis results, illustrated by FIG. 5. As shown, the control has nuclei that are more intensely stained for Oct-1, while A1 has relatively blue nuclei. This is consistent with the Western and Metamorph results.

Figure 6:
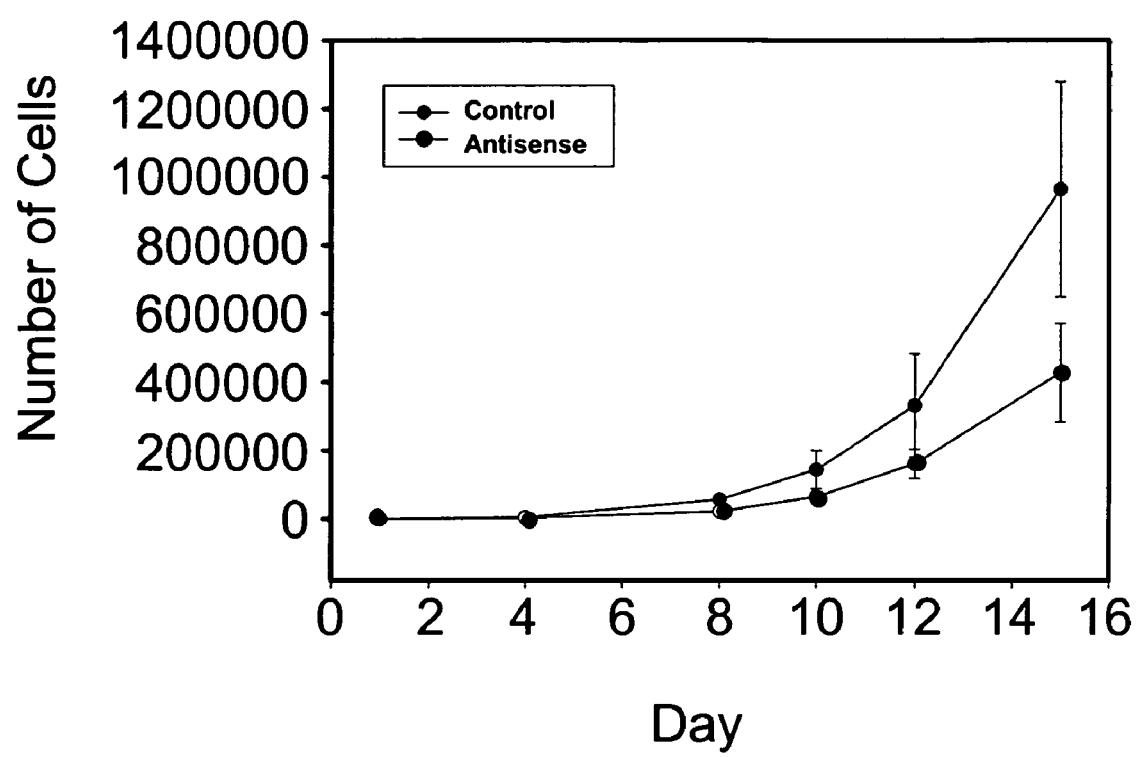
FIG. 6 illustrates the growth rates for Oct-1 antisense transformant A1 and control transformant C1. Similar data was obtained for a second set of transformants, A3 and C2. Combining this data for day fifteen resulted in a p-value of 0.0214.

Four wells were counted per cell line on days four, eight, ten, twelve, and fifteen. Each week, the four counts were averaged to construct growth curves for each clone. Growth rates were graphed for A1 and C1 to visually compare differences, illustrated in FIG. 6. The control transformant C1 had an increased growth rate as compared to A1, with the average number of cells per well consistently greater each week. Similar results were obtained for a second set of clones, A3 and C2. A t-test was conducted using combined data for the two antisense clones versus the two control clones on day fifteen. This test resulted in a p-value of 0.0214, which is considered statistically significant based on rejection of the null hypothesis at a p-value of 0.05 or less.

Figure 7:
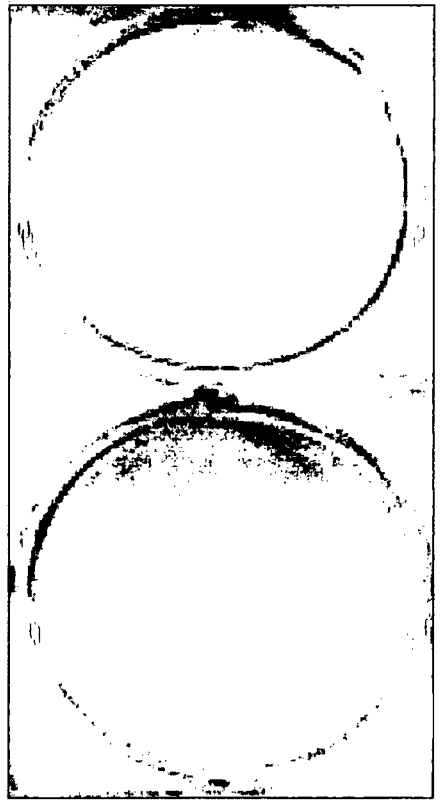
FIG. 7 illustrates a sample of crystal violet stained wells from colonies formed in 0.2% serum for two weeks.
Figure 7:
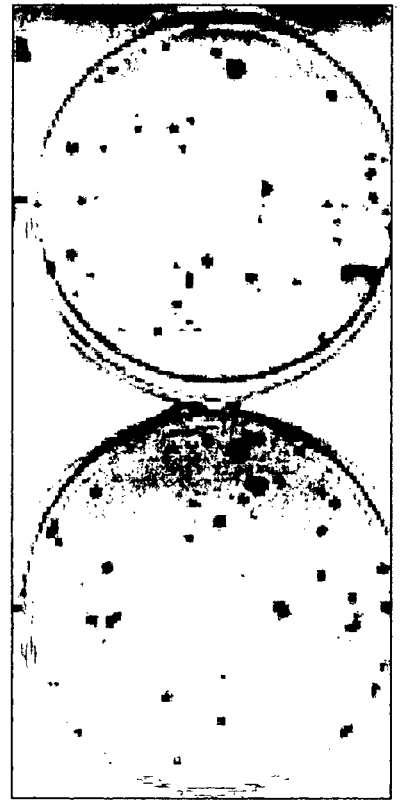
Figure 8:
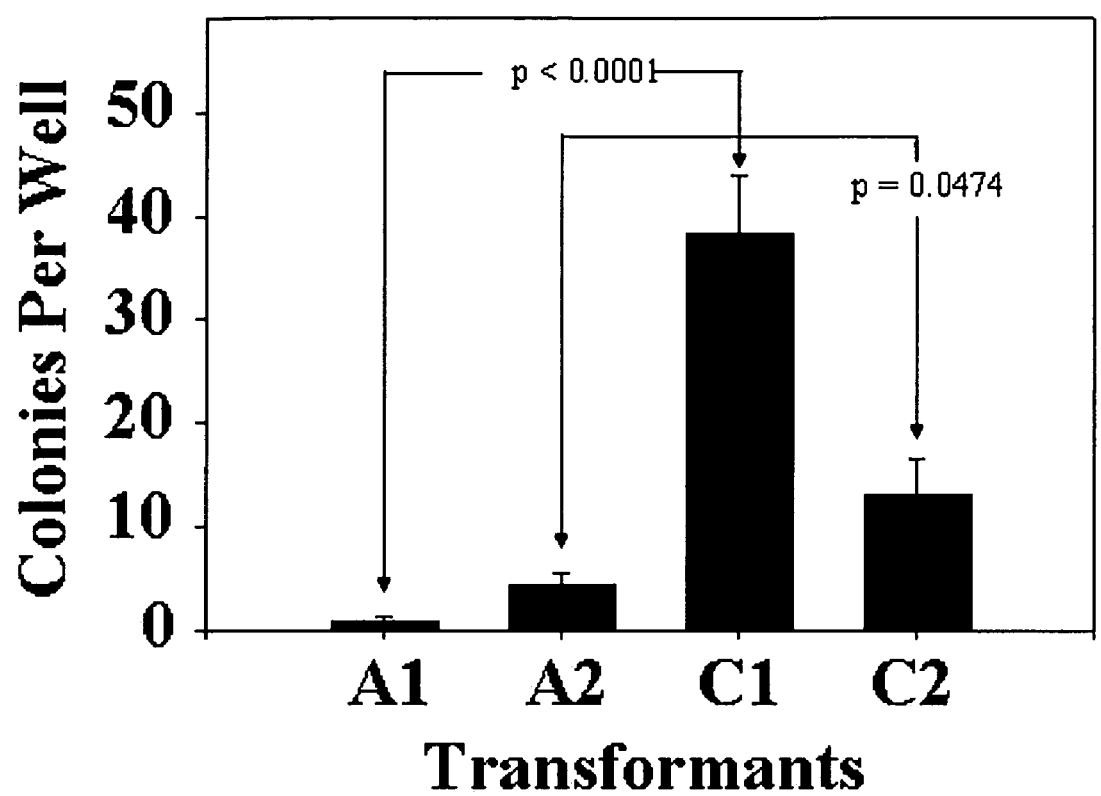
FIG. 8 illustrates the statistical comparison of A1 to C1. Statistical comparison of colony growth in 0.2% serum for Oct-1 antisense transformants A1 and A3, and control transformants C1 and C2. P-values were calculated using a student's t-test.

Oct-1 antisense clones and control clones were grown in 0.2% serum to analyze the effect of the protein's reduction on the need for growth requirements. A comparison of the number of colonies found in Oct-1 antisense versus control transformants revealed a significantly larger number of colonies in the control samples. Specifically, A1 had an average of one colony per well, while C1 had an average of approximately 38 colonies per well, as illustrated by FIG. 7. These values along with those for A3 (4.3 colonies per well) and C2 (13 colonies per well) were graphed and analyzed statistically for significance, as shown in FIG. 8. The difference between A1 and C1 again provided the greatest statistical significance when compared via a t-test. The p-value for this test was less then 0.0001, considered to be an extremely significant deviation. The transformants A3 and C2 resulted in a p-value of 0.0474, which was also statistically significant. This result suggests that the Oct-1 antisense transformants have a less oncogenic phenotype when compared to the control transformants.

The results of the growth curve indicated a decreased growth rate in the antisense transformants as compared to the controls. This is consistent with the idea that the reduction of Oct-1 in the cell produces a less oncogenic phenotype. It was also noted during the growth curve experiment that the control C1 transformants were forming dense foci in colonies as well as at confluence. This overgrowth of the monolayer would be consistent with a loss of contact inhibition and growth arrest for this cell line. No foci formation was noted in the antisense transformants, which would further strengthen the hypothesis of Oct-1's role as an oncoprotein.

The decreased colony formation in 0.2% serum for the Oct-1 antisense transformants was also consistent with a less oncogenic phenotype. The increased colony growth in the control cells implies a reduced need for growth factors and other hormones necessary for cell cycle progression. As growth factors are the stimulus for the start of signal transduction, it would appear that the control cells have bypassed the need for this stimulus and instead have constitutively active signal transduction pathways. The Oct-1 antisense transformants were unable to form colonies in the low serum. Rather, the originally plated cells either died or remained in a static state. Again, this is consistent with a decrease in oncogenicity in these clones.

In the 5637 cell line, there is increased Oct-1 binding activity due to a change in the phosphorylation state. Oct-1 is hypophosphorylated in 5637 cells, which subsequently increases its DNA binding activity. Therefore, these bladder carcinoma cells have an abnormally high level of active Oct-1 as compared to non-cancerous cells. The increased activity of Oct-1 up-regulates the transcription of certain genes, including the H2B histone and possibly DNA synthesis. The altered gene expression drives the cell through the S phase of the cell cycle and results in increased cell division. Also, signal transduction pathways that would normally function to activate the transcription factor may be bypassed due to the dephosphorylated state of Oct-1 in these cells. This would imply a reduced need for growth factors, as was evident in the increased colony formation of the control cells in low serum. The level of active Oct-1 in the 5637 cells receiving the pAS-Oct-1 vector is reduced due to the expression of antisense Oct-1 mRNA. Transcription of the Oct-1 antisense vector therefore acts indirectly to reduce the activity of Oct-1 rather than decreasing binding affinity through phosphorylation. The loss of oncogenic characteristics in the antisense Oct-1 transformants suggests that Oct-1 is a candidate oncoprotein.

While it has been shown that Oct-1 antisense can be used, it is within the scope of the present invention that other modes of inhibiting or eliminating Oct-1 protein, DNA or RNA expression, or DNA-binding capacity can be easily practiced by one of ordinary skill in the art. The invention disclose herein is one embodiment of a detailed description of the activity of Oct-1 in cellular proliferation. Thus, it would be understood by one of ordinary skill in the art that methods to prevent cellular proliferation or tumorigenesis can be practiced by using Oct-1 RNA, DNA, cDNA, or protein molecules in such applications.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be the to fall therebetween. Now that the invention has been described,

What is claimed is:

1. A method for treating a malignant neoplasm in a subject in need thereof, comprising administering to said subject a therapeutically effective amount of an Oct-1 mRNA inhibitor, wherein the Oct-1 inhibitor is a nucleic acid.

2. The method of claim 1 wherein the Oct-1 inhibitor inhibits Oct-1 binding activity.

3. The method of claim 1 wherein the Oct-1 inhibitor inhibits Oct-1 mRNA function.

4. The method of claim 1 wherein the Oct-1 inhibitor is a vector containing an Oct-1 antisense sequence.

5. The method of claim 1 wherein the Oct-1 inhibitor is an RNA inhibitor molecule.

6. The method of claim 1 wherein the Oct-1 inhibitor inhibits Oct-1 mRNA transcription.

7. The method of claim 1 wherein the Oct-1 inhibitor inhibits Oct-1 mRNA translation.

* * * * *